US012653593B2

(12) United States Patent
Glazer et al.

(10) Patent No.: US 12,653,593 B2
(45) Date of Patent: Jun. 16, 2026

(54) IN SITU ROD CUTTERS

(71) Applicant: SG, LLC, Boston, MA (US)

(72) Inventors: Paul Glazer, Boston, MA (US);
Michael J. Milella, Jr., Escondido, CA (US)

(73) Assignee: SG, LLC, Highland Beach, FL (US)

( * ) Notice: Subject to any disclaimer, the term of this patent is extended or adjusted under 35 U.S.C. 154(b) by 634 days.

(21) Appl. No.: 18/081,453

(22) Filed: Dec. 14, 2022

(65) Prior Publication Data

US 2024/0197379 A1     Jun. 20, 2024

(51) Int. Cl.
*A61B 17/88* (2006.01)
*B23D 29/02* (2006.01)

(52) U.S. Cl.
CPC ........ *A61B 17/8863* (2013.01); *B23D 29/023* (2013.01)

(58) Field of Classification Search
CPC .... A61B 17/8863; B23D 21/06; B23D 21/10; B23D 29/02; B23D 29/023; B26B 13/06; B26B 13/12; B26B 13/22; B26B 13/26; B26D 3/169; B26D 7/27
See application file for complete search history.

(56) References Cited

U.S. PATENT DOCUMENTS

| | | | | | |
|---|---|---|---|---|---|
| 401,308 | A | * | 4/1889 | Selleck | B23D 29/023 |
| | | | | | 30/227 |
| 846,629 | A | * | 3/1907 | Sulteen | B26B 13/06 |
| | | | | | 30/254 |

| | | | | | |
|---|---|---|---|---|---|
| 955,287 | A | * | 4/1910 | Schofield | B26B 13/24 |
| | | | | | 30/252 |
| 1,261,134 | A | * | 4/1918 | Klein | B23D 29/023 |
| | | | | | 30/131 |
| 1,319,689 | A | * | 10/1919 | Bernecker | B23D 29/023 |
| | | | | | 30/131 |
| 1,430,705 | A | * | 10/1922 | Wagenbach | B23D 29/023 |
| | | | | | 30/250 |
| 1,469,467 | A | * | 10/1923 | Wagenbach | B23D 17/08 |
| | | | | | 30/250 |
| 1,592,017 | A | * | 7/1926 | Van Campen | B26B 17/02 |
| | | | | | 30/187 |
| 1,643,589 | A | * | 9/1927 | Schwindt | B23D 29/023 |
| | | | | | 30/182 |
| 2,232,315 | A | | 2/1941 | Craig | |
| 2,297,155 | A | * | 9/1942 | Laschinsky | B26B 13/26 |
| | | | | | 30/257 |
| 2,385,835 | A | * | 10/1945 | Neal | B23D 29/023 |
| | | | | | 30/250 |

(Continued)

FOREIGN PATENT DOCUMENTS

| | | | | | |
|---|---|---|---|---|---|
| CN | | 106109002 A | * | 11/2016 | ........ A61B 17/8863 |
| CN | | 116727753 A | * | 9/2023 | ............ B23D 29/02 |

*Primary Examiner* — Jason Daniel Prone
(74) *Attorney, Agent, or Firm* — Troutman Pepper Locke LLP; Joshua L. Jones; Gabrielle L. Gelozin

(57) ABSTRACT

In accordance with at least one aspect of this disclosure, a surgical rod cutter assembly includes a first blade member including a first open notch in a first end thereof. The first open notch spans across a first ingress axis, along which a rod is inserted for cutting. A first rotation bore is defined through the first blade member, a linkage of the first blade member extends away from the rotation bore on a first linkage axis, and the first rotation bore intersects the first linkage axis.

20 Claims, 9 Drawing Sheets

(56) References Cited

U.S. PATENT DOCUMENTS

| | | | | |
|---|---|---|---|---|
| 2,428,650 A * | 10/1947 | Brunner | B23D 29/023 | 83/199 |
| 2,502,582 A * | 4/1950 | Murphy et al. | B23D 29/023 | 30/142 |
| 2,915,820 A * | 12/1959 | Naito | B23D 29/023 | 30/227 |
| 2,915,822 A * | 12/1959 | Naito | B23D 29/023 | 30/250 |
| 2,932,224 A | 4/1960 | Peed et al. | | |
| 2,993,275 A * | 7/1961 | Naito | B23D 29/023 | 30/250 |
| 3,047,947 A | 8/1962 | Spenninger | | |
| 3,170,237 A * | 2/1965 | Weidauer | B26B 13/28 | 30/267 |
| 3,370,353 A * | 2/1968 | Weissman et al. | B23D 29/023 | 30/131 |
| 3,716,879 A * | 2/1973 | Boyajian | B23D 29/023 | 30/194 |
| 3,996,782 A * | 12/1976 | Sgariglia | B23D 17/06 | 30/250 |
| 4,058,893 A * | 11/1977 | Boyajian | B23D 29/023 | 30/189 |
| 4,069,582 A * | 1/1978 | Kearns | B26B 17/02 | 30/182 |
| 4,249,308 A * | 2/1981 | Boyajian | B23D 29/023 | 30/260 |
| 4,271,593 A * | 6/1981 | Smith | B23D 29/023 | 30/233 |
| 4,347,724 A | 9/1982 | Brown et al. | | |
| 4,439,923 A * | 4/1984 | Scranton | B26B 13/26 | 30/252 |
| 4,759,671 A * | 7/1988 | Duran | F16B 21/125 | 411/347 |
| 4,868,986 A * | 9/1989 | Olson | B26B 17/003 | 30/193 |
| 5,099,577 A * | 3/1992 | Hutt | B26D 3/169 | 30/97 |
| 5,187,869 A * | 2/1993 | Heiss | A61B 17/8863 | 30/189 |
| 5,261,303 A * | 11/1993 | Strippgen | B23D 29/023 | 83/200 |
| 5,836,937 A * | 11/1998 | Holmes | A61B 17/8863 | 30/179 |
| 5,988,027 A * | 11/1999 | Lenox | A61B 17/8863 | 83/699.61 |
| 6,058,820 A * | 5/2000 | Rinner | B23D 29/023 | 30/253 |
| 6,085,425 A | 7/2000 | Weber | | |
| 6,088,920 A * | 7/2000 | Schmick | B23D 29/023 | 30/252 |
| 6,185,825 B1 * | 2/2001 | Olson | B23D 29/023 | 30/90.1 |
| 6,574,870 B1 * | 6/2003 | Huang | B23D 29/02 | 30/252 |
| 7,191,525 B2 | 3/2007 | Brailovskiy | | |
| 7,690,118 B2 * | 4/2010 | Yamakado | B23D 29/023 | 30/189 |
| 7,690,119 B1 * | 4/2010 | Weber | B23D 29/02 | 30/192 |
| 7,913,400 B2 * | 3/2011 | Larkin | B26B 17/02 | 30/235 |
| 8,127,454 B1 * | 3/2012 | Gao | B23D 29/023 | 30/92 |
| 8,413,555 B2 * | 4/2013 | Farrell | B23D 29/023 | 7/117 |
| 8,601,923 B1 * | 12/2013 | Gao | B23D 29/023 | 30/92 |
| 8,714,427 B2 * | 5/2014 | McClintock | A61B 17/8863 | 225/2 |
| 9,144,447 B2 * | 9/2015 | McClintock | A61B 17/8863 | |
| 9,457,414 B2 * | 10/2016 | Merz | A61B 17/8863 | |
| 10,905,488 B2 * | 2/2021 | Rinner | B26B 13/26 | |
| 12,156,681 B2 * | 12/2024 | Ludwig | A61B 50/20 | |
| 2006/0130343 A1 | 6/2006 | Simcoe | | |
| 2007/0019401 A1 * | 1/2007 | Liebowitz | B26B 13/22 | 362/115 |
| 2008/0000091 A1 * | 1/2008 | Eriguchi | B23D 29/023 | 30/92 |
| 2008/0005910 A1 * | 1/2008 | Hsiao | B23D 29/023 | 30/252 |
| 2008/0178707 A1 | 7/2008 | Stevens | | |
| 2010/0236080 A1 * | 9/2010 | Huang | B23D 29/023 | 30/251 |
| 2013/0213202 A1 | 8/2013 | Crainich | | |
| 2020/0022771 A1 * | 1/2020 | Chapolini | A61B 50/00 | |
| 2022/0111452 A1 * | 4/2022 | Caglar | B26B 13/26 | |
| 2023/0061887 A1 * | 3/2023 | Joly | A61B 17/8863 | |
| 2024/0058046 A1 * | 2/2024 | Melnick | A61B 17/8863 | |

* cited by examiner

IN SITU ROD CUTTERS

BACKGROUND

1. Field

The present disclosure relates to surgical instruments, and more particularly to rod cutters such as used for cutting rods in orthopedic surgical procedures.

2. Description of Related Art

During some orthopedic procedures, metal rods are used to stabilize bones. For example, two or more pedicle screws can be connected with a metal rod to stabilize two or more vertebra together. The rod must be long enough to connect to each pedicle screw, but needs to be short enough not to cause complications by extending significantly beyond the pedicle screws. This rod length is not known before a procedure, and is unique to each patient. Therefore, typical procedures call for an iterative process of fitting the rod in place near or in the pedicle screws, observing its excess length, removing excess length from the rod using a rod cutter outside the surgical site, then replacing the cut rod back near or in the pedicle screws and repeating if necessary. If the rod is ever cut too short to bridge the pedicle screws, the process must be restarted with a new rod, so surgeons tend to remove length from the rod conservatively in each iteration. Since the iterative process adds time to the surgery and can add trauma to the tissues of the surgical site, it would be desirable to eliminate the iterations so that a rod can be cut to the proper length on the first cut.

The conventional techniques have been considered satisfactory for their intended purpose. However, there is an ever present need for improved systems and methods for rod cutting, e.g. in orthopedic surgical settings. This disclosure provides a solution for this need.

SUMMARY

In accordance with at least one aspect of this disclosure, a surgical rod cutter assembly includes a first blade member including a first open notch in a first end thereof. The first open notch spans across a first ingress axis, along which a rod is inserted for cutting. A first rotation bore is defined through the first blade member, a linkage of the first blade member extends away from the rotation bore on a first linkage axis, and the first rotation bore intersects the first linkage axis.

The surgical rod cutter assembly includes a second blade member including a second open notch in a first end thereof. The second open notch spans across a second ingress axis, along which the rod is inserted for cutting. A second rotation bore is defined through the second blade member, a linkage of the second blade member extends away from the rotation bore on a second linkage axis, and the second rotation bore intersects the second linkage axis.

A fulcrum pin is engaged through the first and second rotation bores to rotationally engage the first and second blade members together in an open position and a closed position. In the open position, the first and second ingress axes are aligned with one another to admit a rod therealong into the first and second open notches for cutting. Still in the open position, the first and second linkage axes are angled to a narrow position relative to one another. In the closed position, the first and second ingress axes are angled relative to one another, and first and second linkage axes are angled at a widened position relative to the narrow position to grasp/cut the rod therein. In embodiments, in both the open position and in the closed position, the first and second ingress axes both pass through a rotation axis that extends along the fulcrum pin.

In embodiments, the first open notch can include a first notch surface on one side of the first ingress axis, a second notch surface opposite the first notch surface across the first ingress axis, and a terminal surface connecting between the first and second notch surfaces, terminating the first open notch along the first ingress axis. The first open notch can define an opening between the first and second notch surfaces that opens away from the fulcrum pin. In certain embodiments, the first and second notch surfaces of the first open notch can be parallel to one another, and the terminal surface of the first open notch can be semi-cylindrical or otherwise conformal to a shape of the rod.

In embodiments, the second open notch can include a first notch surface on one side of the second ingress axis, a second notch surface opposite the first notch surface across the second ingress axis, and a terminal surface connecting between the first and second notch surfaces, terminating the second open notch along the second ingress axis. The second open notch can define an opening between the first and second notch surfaces that opens away from the fulcrum pin. In certain embodiments, the first and second notch surfaces of the second open notch can be parallel to one another and the terminal surface of the second open notch can be semi-cylindrical. In certain embodiments, the terminal surface of the second open notch can be symmetrical or identical to terminal surface of the first open notch, or otherwise conformal to a shape of the rod.

In embodiments, in the open position, the first notch surface of the first open notch can be aligned parallel (e.g., coplanar) with the first notch surface of the second open notch, the second notch surface of the first open notch can be aligned parallel (e.g., coplanar) with the second notch surface of the second open notch, and in the open position, the first ingress axis can be aligned (e.g., parallel) with the second ingress axis. In certain embodiments, the first and second blade members can each have a facet at a distal end thereof configured to assist in urging the rod into the first and second open notches in the open position. In embodiments, in the closed position, the first and second ingress axes can be angled obliquely relative to one another and in the closed position, the first and second open notches are misaligned for holding a cut rod piece.

In embodiments, the first blade member can include a first pawl extending into a pocket of the second blade member, wherein in the closed position, the first pawl cooperates with the terminal surface of the second open notch to form a capture pocket configured to capture a cut rod piece after cutting a rod. The pawl extends from the shearing surface of the first blade member in a direction parallel to the axis of rotation of the fulcrum pin. The first pawl can include a capture surface that is cylindrical configured to surround a majority of the circumference of the cut rod piece in cooperation with the terminal surface of the second open notch.

In embodiments, the second blade member can include a second pawl extending into a pocket of the first blade member, wherein in the closed position, the second pawl cooperates with the terminal surface of the first open notch to form a capture pocket configured to capture a cut rod piece after cutting a rod. The pawl extends from the shearing surface of the second blade member in a direction parallel to the axis of rotation of the fulcrum pin. The second pawl can include a capture surface that is cylindrical configured to surround a majority of the circumference of the cut rod piece in cooperation with the terminal surface of the first open notch.

A bearing washer can extend around the fulcrum pin and rotatably engaged to inward facing bearing surfaces of each of the first and second blade members. In embodiments, a first outside washer can be engaged to the fulcrum pin and an outer surface of the first blade member and a second outside washer can be engaged to the fulcrum pin and an outer surface of the second blade member.

In embodiments, the assembly can include an actuator tool. In certain embodiments, the actuator tool can include a first linkage including a first handle portion, a first main pin bore, and a first linkage bore. The actuator tool can further include a second linkage including a second handle portion, a second main pin bore, and a second linkage bore. The first and second linkages can be joined to one another by a main pin engaged through the first and second main pin bores for relative rotation. The first linkage can be pinned with a first linkage pin that passes through the first linkage bore and a corresponding bore of the first blade member and the second linkage can be pinned with a second linkage pin that passes through the second linkage bore with a corresponding bore of the second blade member. In certain embodiments, the first and second linkages can be configured so that in the first position of the blade members, actuating the first and second handle portions together moves the first and second linkage pins away from one another to move the first and second blade members toward the second position.

In embodiments, the first linkage pin can be removably engaged to the first linkage and to the first blade member with a movable detent ball in the first linkage pin. The second linkage pin can be removably engaged to the second linkage and to the second blade member with a movable detent ball in the second linkage pin.

In embodiments the assembly can further include a threaded rod connecting the first handle portion to the second handle portion. In certain embodiments, a knob can be operatively connected to the threaded rod to actuate the first and second linkages between the first and second positions. In certain embodiments, the knob can include one or more leveraging bores configured to receive a lever arm to facilitate rotation of the knob.

In accordance with at least one aspect of this disclosure, a kit can include a package having a sterile interior. The package can enclose a first blade member including a first open notch in a first end thereof, wherein the first open notch spans across a first ingress axis along which a rod is inserted for cutting, wherein there is a first rotation bore defined through the first blade member, wherein a linkage of the first blade member extends away from the rotation bore on a first linkage axis, and wherein the first rotation bore intersects the first linkage axis.

The package can also enclose a second blade member including a second open notch in a first end thereof, wherein the second open notch spans across a second ingress axis along which a rod is inserted for cutting, wherein there is a second rotation bore defined through the second blade member, wherein a linkage of the second blade member extends away from the rotation bore on a second linkage axis, and wherein the second rotation bore intersects the second linkage axis. The package can include a fulcrum pin configured to be engaged through the first and second rotation bores to rotationally engage the first and second blade members together.

In certain embodiments, the first and second blade members can be identical to one another. In embodiments, a pair of ball detent pins can be enclosed in the package, configured to join the first and second blade members to an actuator tool. In embodiments, the actuator tool can also be enclosed in the package. In embodiments, a leveraging member can be included in the package configured to engage a threaded rod knob of the actuator tool to provide leverage for actuating the first and second blade members.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
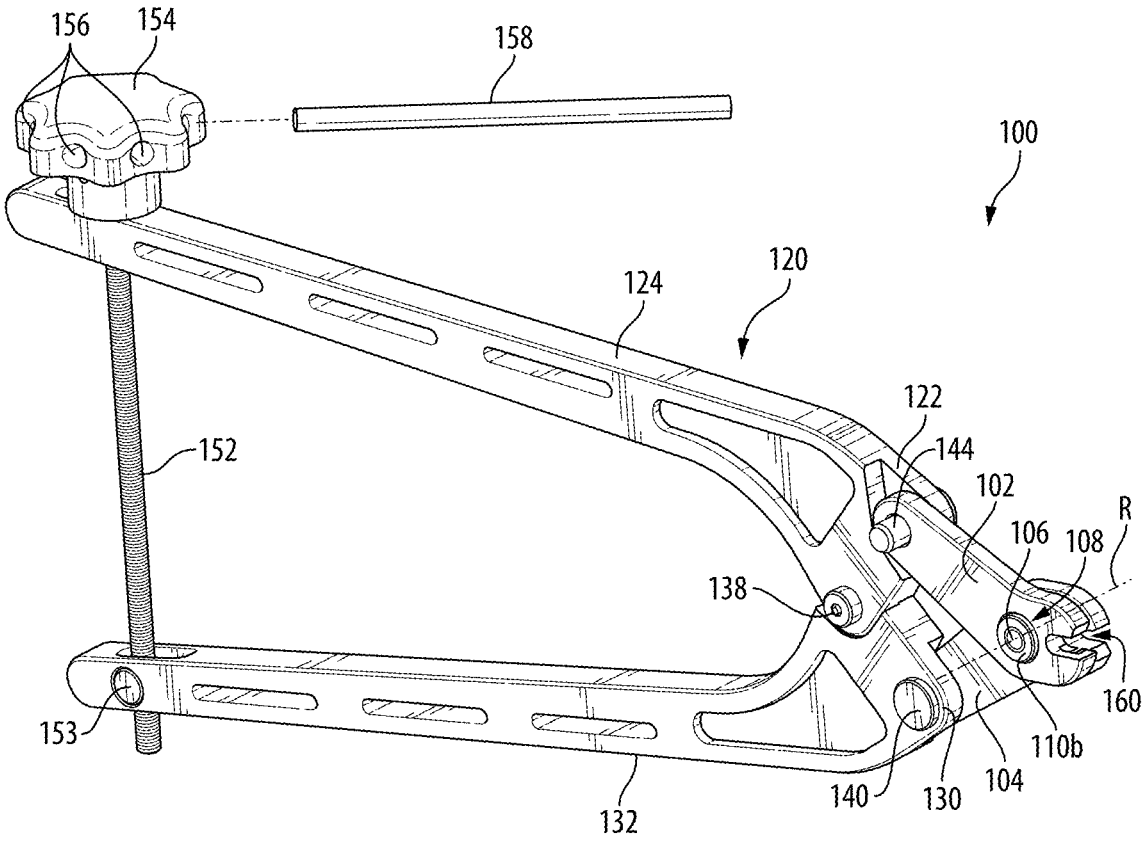
FIG. 1 is a perspective view of an embodiment of an assembly constructed in accordance with the present disclosure, showing an in-situ rod cutter.
Figure 2:
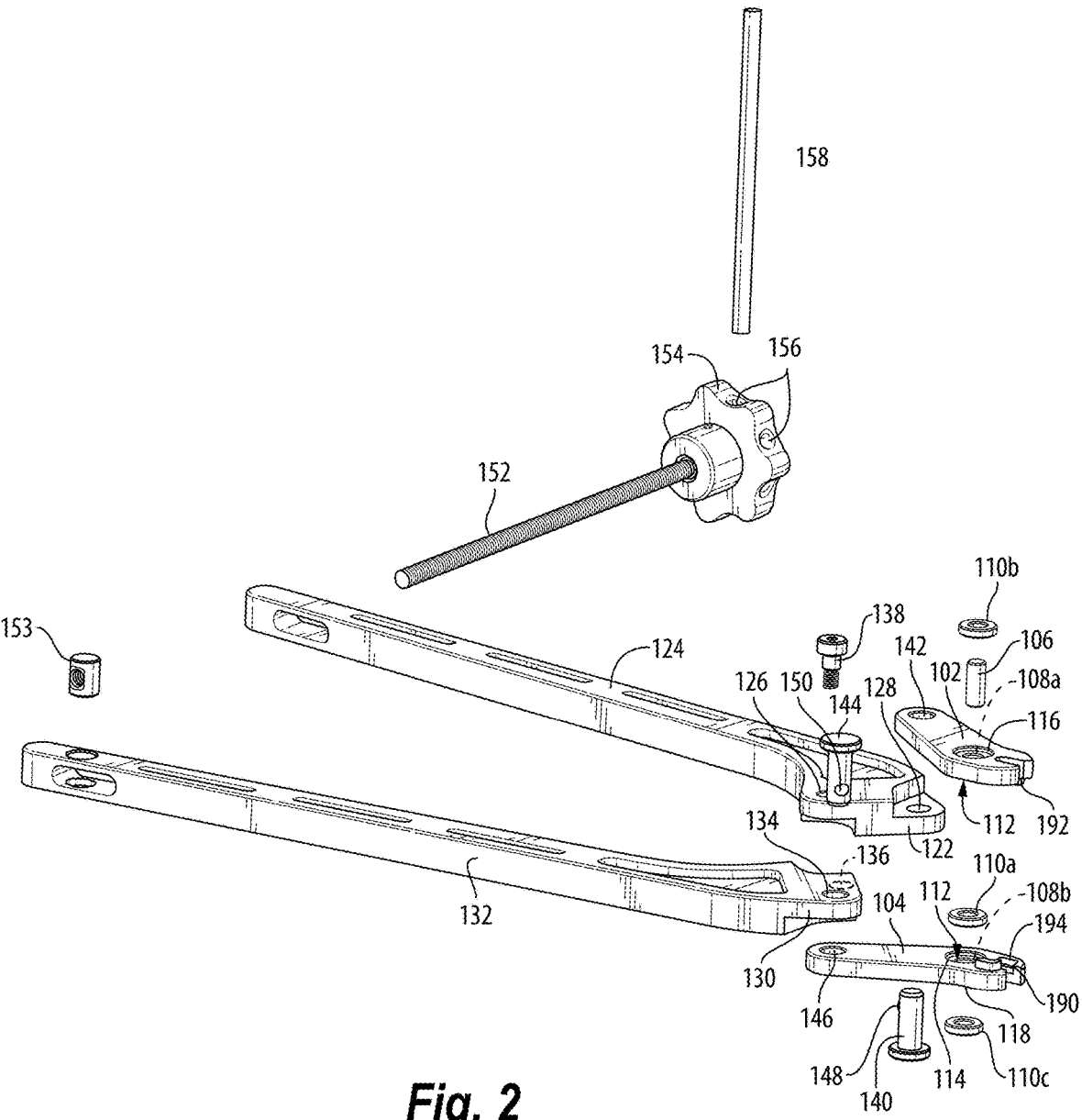
FIG. 2 is a an exploded perspective view of the assembly of FIG. 1.

Reference will now be made to the drawings wherein like reference numerals identify similar structural features or aspects of the subject disclosure. For purposes of explanation and illustration, and not limitation, a partial view of an embodiment of an assembly in accordance with the disclosure is shown in FIG. 1 and is designated generally by reference character 100. Other embodiments of systems in accordance with the disclosure, or aspects thereof, are provided in FIGS. 2-13B, as will be described. The systems and methods described herein can be used to cut a surgical rod.

In accordance with at least one aspect of this disclosure, and with reference to FIGS. 1-6 a surgical rod cutter assembly 100 includes a first blade member 102 and a second blade member 104 coupled via a fulcrum pin 106 engaged through a respective rotation bore 108a,b defined in each of the first and second blade members 102, 104 to form a main rotation bore 108.

One or more washers 110,a,b,c, can be included along the fulcrum pin 106. A bearing washer 110a can be seated in a washer seat 112 defined at least partially in both the first and second blade members 102, 104 so that the first and second blade members 102, 104 sandwich the bearing washer 110a. The bearing washer 110a can extend around the fulcrum pin 106 and rotatably engaged an inward facing bearing surface 114 of each of the first and second blade members 102, 104. In embodiments, a first outside washer 110b can be engaged to the fulcrum pin 106 and an outer surface 116 of the first blade member 102 and a second outside washer 110c can be engaged to the fulcrum pin 106 and an outer surface 118 of the second blade member 104. In certain embodiments, the assembly 100 may not include either of washers 110a, 110c.

Referring to FIGS. 1-4, in embodiments, the assembly 100 can include actuator tool 120. The actuator tool 120 can include a first linkage 122 including a first handle portion 124, a first main pin bore 126, and a first linkage bore 128. The actuator tool 120 can further include a second linkage 130 including a second handle portion 132, a second main pin bore 134, and a second linkage bore 136, which is shown in dotted lines since it is obscured by the linkage 130. The first and second linkages 122, 130 can be joined to one another by a main pin 138 engaged through the first and second main pin bores 126, 134 for relative rotation. The first linkage 122 can be pinned with a first linkage pin 144 that passes through the first linkage bore 128 and a corresponding bore 142 of the first blade member 102 and the second linkage 130 can be pinned with a second linkage pin 140 that passes through the second linkage bore 136 and a corresponding bore 146 of the second blade member 104. In certain embodiments, the first and second linkages 122, 130 can be configured so that in the first position of the blade members 102, 104, actuating the first and second handle portions 124, 132 together moves the first and second linkage pins 144, 140 away from one another to move the first and second blade members 102, 104 toward the second position (e.g., as best seen in comparing FIGS. 3 and 4, where the heavy arrows indicate motion directions at different positions in the handle portions 124, 132 in moving from the position of FIG. 3 into the position of FIG. 4).

In embodiments, the first linkage pin 144 can be removably engaged to the first linkage 122 and to the first blade member 102 with a movable detent ball 150 in the first linkage pin 144. The second linkage pin 140 can be removably engaged to the second linkage 130 and to the second blade member 104 with a movable detent ball 148 in the second linkage pin 140. The assembly 100 can further include a threaded rod 152 connecting the first handle portion 124 to the second handle portion 132. The threaded rod 152 can move freely in an aperture defined within the first handle member 124 and can rock via a pivoting worm nut 153 in the second handle portion 132 as the first and second handle members 124, 132 come together and move away from one another. In certain embodiments, a knob 154 can be operatively connected to the threaded rod 152 to actuate the first and second linkages 122, 130 between the first and second positions. In certain embodiments, the knob 154 can include one or more leveraging bores 156 configured to receive a lever arm 158 to facilitate rotation of the knob 154.

Referring now to FIGS. 3-6, the first blade member 102 includes a first open notch 160 in a first end 162 thereof, the first open notch 160 spanning across a first ingress axis A, along which a rod 164 is inserted for cutting. For clarity and ease of understanding the rod 164 is not shown in FIGS. 3-6, but is shown in FIGS. 7-12. A linkage 166 of the first blade member 102 extends away from the first rotation bore 108a on a first linkage axis C where the first rotation bore 108a intersects the first linkage axis C. In embodiments, the second blade member 104 can be the same or similar to the first blade member 102, where the second blade member 104 can include a second open notch 168 in a first end 170 thereof, the second open notch 168 spanning across a second ingress axis B, along which the rod 164 is inserted for cutting. For clarity and ease of understanding the rod 164 is not shown in FIGS. 3-6, but is shown in FIGS. 7-12. A linkage 172 of the second blade member 104 extends away from the second rotation bore 108b on a second linkage axis D where the second rotation bore 108b intersects the second linkage axis D. The fulcrum pin 106 is engaged through the first and second rotation bores 108a,b to rotationally engage the first and second blade members 102, 104 together in both an open position and a closed position.

Figures 3, 4:
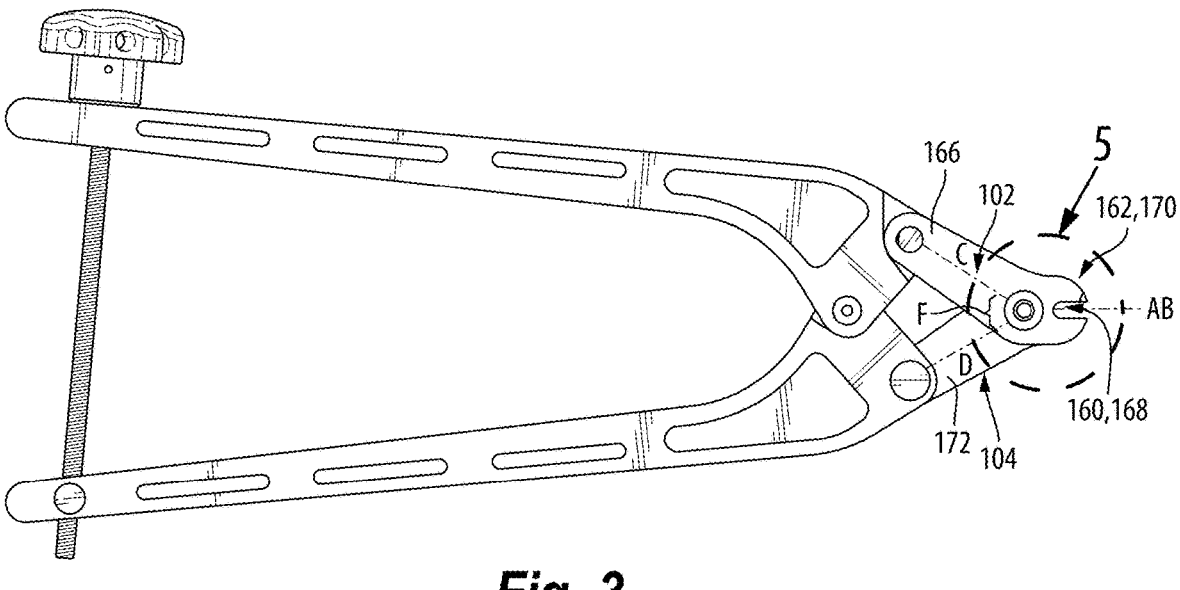
FIG. 3 is a side view of the assembly of FIG. 1, showing the in-situ rod cutter in a first position.
FIG. 4 is a side view of the assembly of FIG. 1, showing the in-situ rod cutter in a second position.
Figure 5:
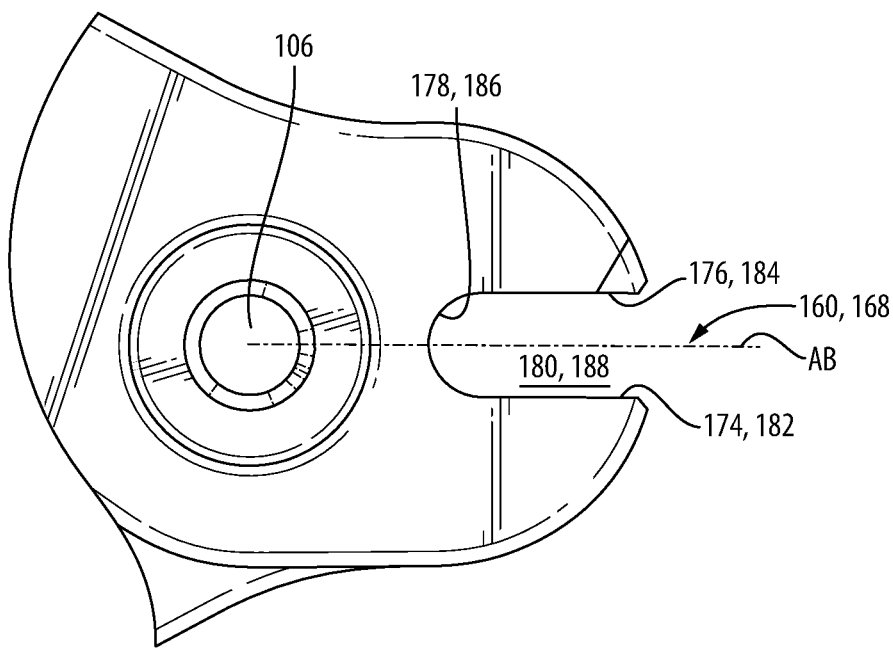
FIG. 5 is an enlarged partial view of a first and second blade members of the rod cutter of FIG. 3, shown in the first position.
Figure 6:
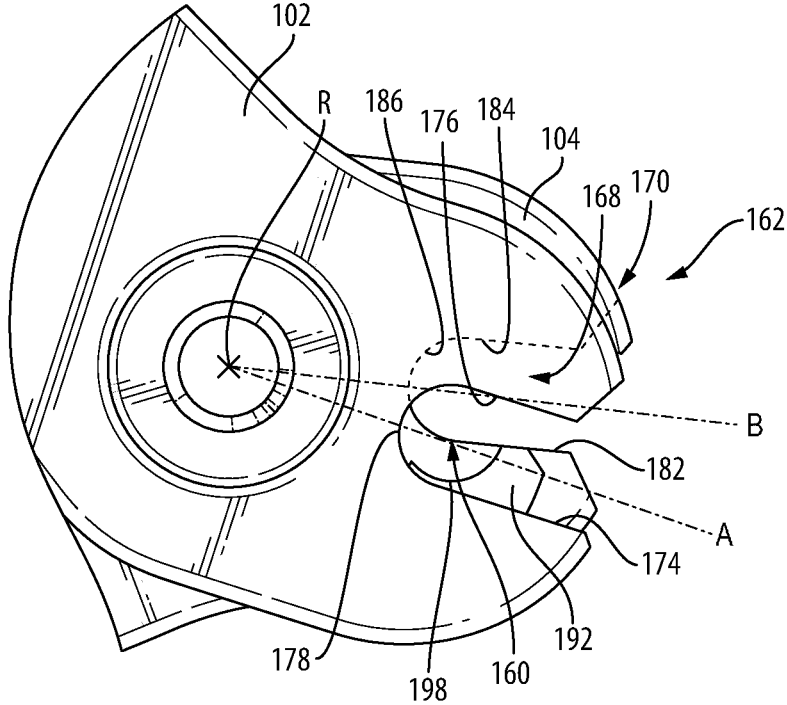
FIG. 6 is an enlarged partial view of a first and second blade members of the rod cutter of FIG. 4, shown in the second position.
Figure 7:
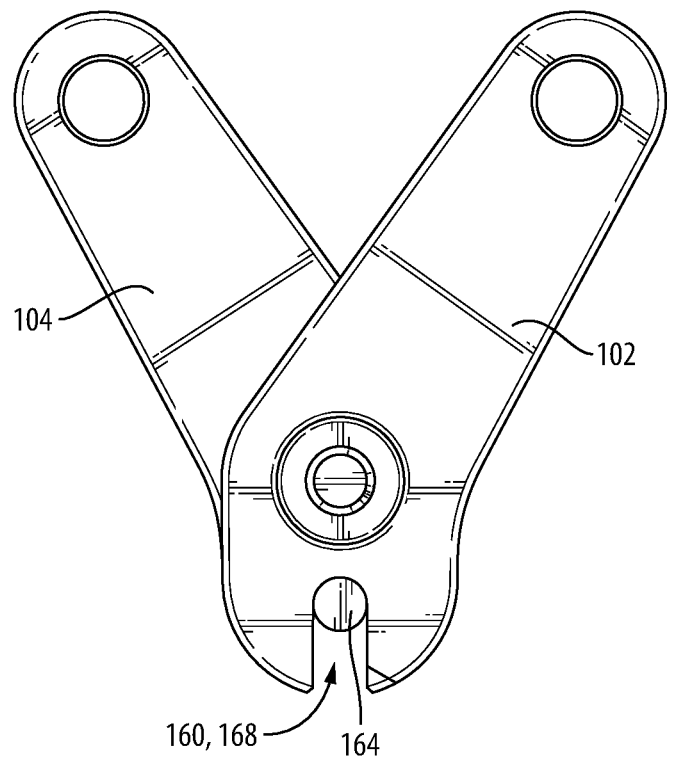
FIG. 7 is top plan view of the first and second blade members coupled via fulcrum pin.
Figure 8:
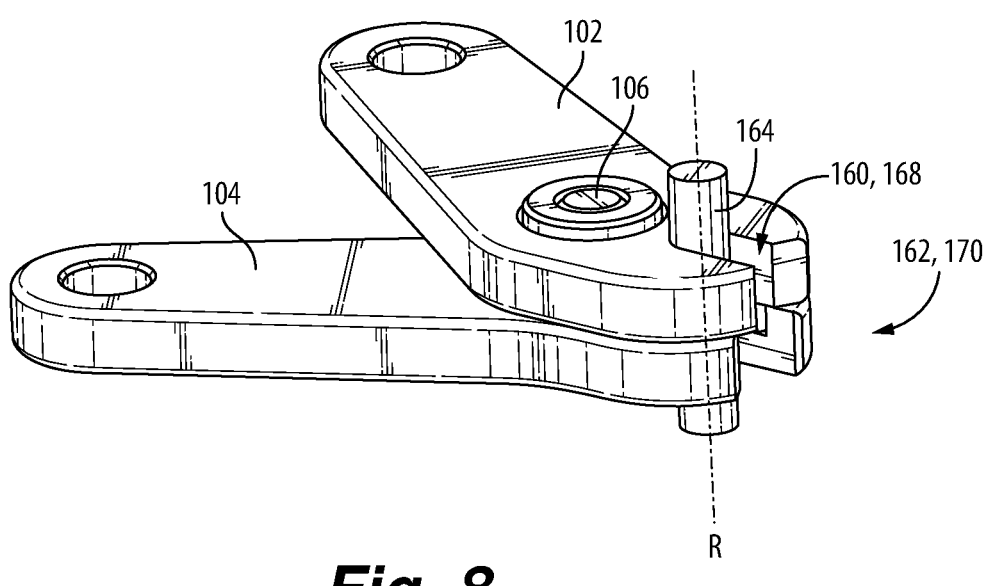
FIG. 8 is a perspective view of the first and second blade members of FIG. 7, showing the first and second blade members engaging a piece of rod to be cut.
Figure 9:
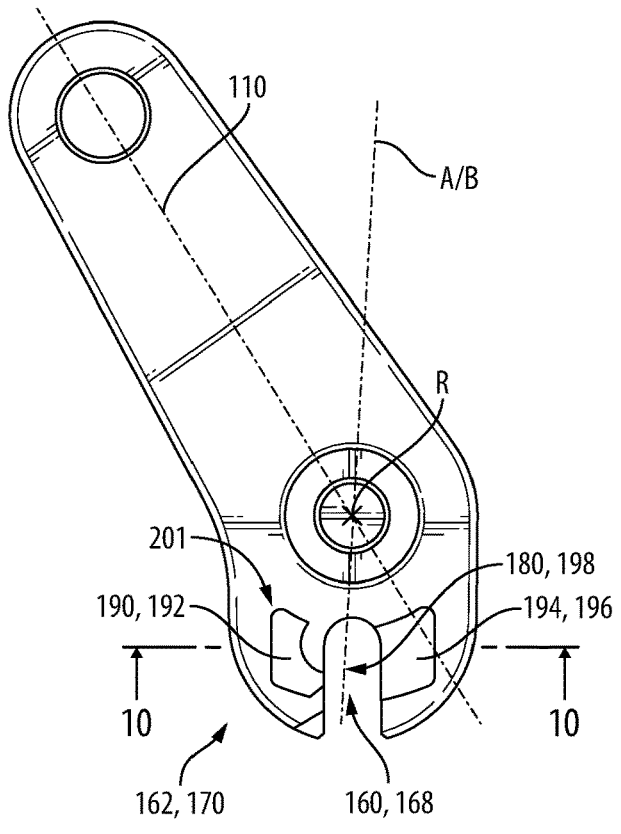
FIG. 9 is a bottom plan view of the first or second blade member showing a pawl and corresponding pawl pocket.

In the open position, the first and second ingress axes A, B are aligned with one another to admit the rod therealong into the first and second open notches 160, 168 for cutting (e.g., as shown in FIGS. 3 and 5). Still in the open position, the first and second linkage axes C, D are angled at angle F to a narrow position relative to one another (e.g., as shown in FIGS. 3 and 5). In the closed position, the first and second ingress axes A, B are angled relative to one another, and first and second linkage axes C, D are angled at and G, where the angle G of the closed position is greater than the angle F of the narrower, open position to grasp/cut the rod 164 therein (e.g., as shown in FIGS. 4 and 6). In embodiments, in both the open position and in the closed position, the first and second ingress axes C, D both pass through a rotation axis R that extends along the fulcrum pin 106.

With reference to FIGS. 3 and 5 specifically, in embodiments, the first open notch 160 can include a first notch surface 174 on one side of the first ingress axis A, a second notch surface 176 opposite the first notch surface 174 across the first ingress axis A, and a terminal surface 178 connecting between the first and second notch surfaces 174, 176, terminating the first open notch 160 along the first ingress axis A. The first open notch 160 can define an opening 180 between the first and second notch surfaces 174, 176 that opens away from the fulcrum pin 106. In certain embodiments, the first and second notch surfaces 174, 176 of the first open notch 160 can be parallel to one another, and the terminal surface 178 of the first open notch 160 can be semi-cylindrical (e.g., as shown) or otherwise conformal to a shape of the rod 164. The second open notch 168 of the second blade member 104 can be the same or similar to that of the first blade member 102. In FIGS. 3 and 5, the first and second blade members 102, 104 are aligned such that the first and second open notches 160, 168 are stacked and the second open notch 168 is out of view.

The second open notch 168 can include a first notch surface 182 on one side of the second ingress axis B, a second notch surface 184 opposite the first notch surface 182 across the second ingress axis B, and a terminal surface 186 connecting between the first and second notch surfaces 182, 184, terminating the second open notch 168 along the second ingress axis B. The second open notch 168 can define an opening 188 between the first and second notch surfaces 182, 184 that opens away from the fulcrum pin 106. In certain embodiments, the first and second notch surfaces 182, 184 of the second open notch 168 can be parallel to one another and the terminal surface 186 of the second open notch 168 can be semi-cylindrical. In certain embodiments, the terminal surface of the second open notch can be symmetrical or identical to terminal surface of the first open notch 160 (e.g., as shown), or otherwise conformal to a shape of the rod 164. FIGS. 4 and 6 show the blade members 102, 104 in the closed position, where the ingress axes A, B are misaligned, and at least the first notch surface 182 of the second open notch 168 can be seen in view.

As shown in FIG. 5, in the open position, the first notch surface 174 of the first open notch 160 can be aligned parallel (e.g., coplanar) with the first notch surface 182 of the second open notch 168 and the second notch surface 176 of the first open notch 160 can be aligned parallel (e.g., coplanar) with the second notch surface 184 of the second open notch 168. Also in the open position, the first ingress axis A can be aligned (e.g., parallel) with the second ingress axis B. As shown in FIG. 6, in the closed position, the first and second ingress axes A, B can be angled obliquely relative to one another and in the closed position, the first and second open notches 160, 168 are misaligned for holding the cut rod piece.

Figure 10:
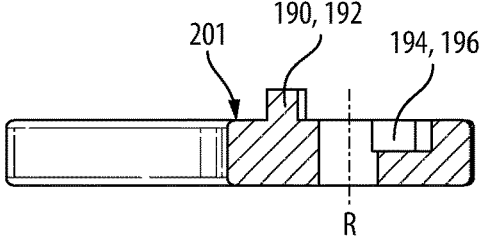
FIG. 10 is a cross sectional view of the first or second blade member of FIG. 9, showing the pawl and corresponding pawl pocket.
Figure 11:
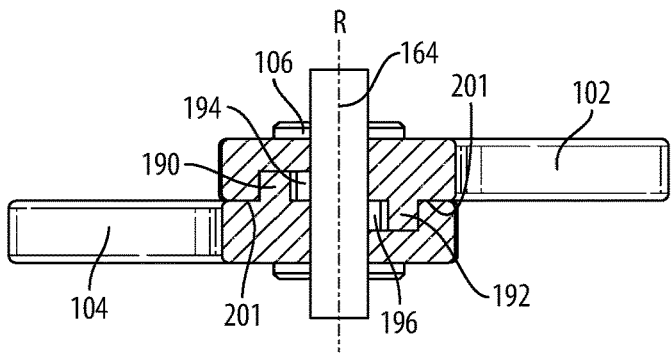
FIG. 11 is a front end cross sectional view of the first and second blade members engaging a piece of rod to be cut.

With reference now to FIGS. 6-11, in embodiments, the first blade member 102 and the second blade member 104 can each include a respective pawl 190, 192 and a respective pawl pocket 194, 196 configured to engage with one another. The respective pawl 190, 192 extends from a shearing surface 201 of the first and second blade members 102, 104 in a direction parallel to the axis of rotation R of the fulcrum pin 106 (e.g., as seen in FIGS. 10 and 11). When the assembly 100 is assembled, the pawl 192 of the first blade member 102 can extend into the pawl pocket 196 of the second blade member 104 and the pawl 190 of the second blade member 104 can extend into the pawl pocket 194 of the first blade member 102 (e.g., as best seen in FIG. 11). In the closed position, the pawl 190 of the second blade member 104 cooperates with the terminal surface 178 of the first open notch 160 to form a capture pocket 198 configured to capture the cut rod piece after cutting the rod, so that the cut piece of rod does not move or otherwise get lost in the surgical field or within the patient. The capture pocket 198 can best be seen in the enlarged view of FIG. 6. At the same time, (out of view in FIG. 6, but seen more clearly in FIG. 12), the pawl 192 of the first blade member 102 cooperates with the terminal surface 186 of the second open notch 168 to form a capture pocket to maintain a grip on the portion of the rod 164 that remains in situ after the rod is cut. This cut piece of rod that is removed is on the opposite side of the assembly of that shown in FIG. 6, for example. Once the rod 164 has been cut, the rod cutter assembly 100, while still holding onto the cut piece of rod 164', can be removed from the installed rod 164 and surgical cavity. The capture surface or pocket 198 can be cylindrical to surround a majority of the circumference of the cut rod piece 164' in cooperation with the terminal surface of the open notch of the cooperating blade member (e.g., the terminal surface 178 of the first open notch 160 as seen in FIG. 6).

Figure 12:
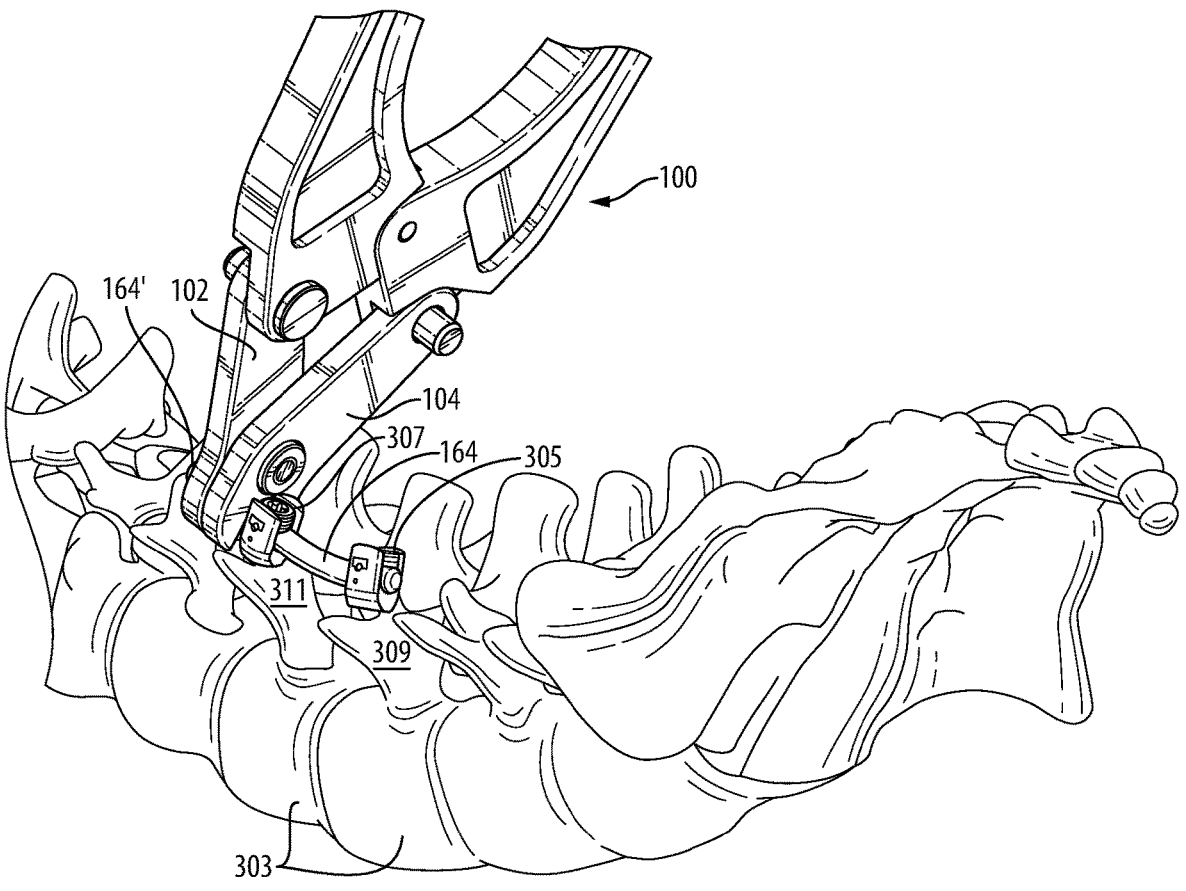
FIG. 12 is a perspective view of a surgical procedure, showing the in-situ rod cutter of FIG. 1 cutting a rod in-situ.

FIG. 12), the pawl 190 of the first blade member 102 cooperates with the terminal surface 186 of the second open notch 168 to form a capture pocket to maintain a grip on the portion of the rod 164 that remains in situ after the rod is cut. This cut piece of rod that is removed is on the opposite side of the assembly of that shown in FIG. 6, for example. Once the rod 164 has been cut, the rod cutter assembly 100, while still holding onto the cut piece of rod 164', can be removed from the installed rod 164 and surgical cavity. The capture surface or pocket 198 can be cylindrical to surround a majority of the circumference of the cut rod piece 164' in cooperation with the terminal surface of the open notch of the cooperating blade member (e.g., the terminal surface 178 of the first open notch 160 as seen in FIG. 6).

FIG. 12 shows the rod cutter assembly 100 cutting a rod 164 in-situ during an orthopedic surgical procedure. When performing certain procedures, such as to stabilize two or more vertebra 303 together, a surgeon will first insert one or more pedicle screws 305, 307 into respective pedicles 309, 311 of a patient's spine. The surgeon will then insert the rod 164 between the pedicles screws 305, 307 to fix the position of the respective pedicles 309, 311 relative to one another. Because the rod length necessary for the procedure is not known prior to insertion between the pedicle screws, any excess rod 164' can then be cut from surgical site using the rod cutter assembly 100 as discussed herein. The rod cutter assembly 100 is configured and adapted to cut any excess rod 164' from the surgical site and maintain the cut piece of rod 164' within the rod cutter 100 (e.g., with a respective pawl of a respective blade member capture pocket) so that the cut piece of rod 164' does not get lost in the surgical site or remain in the patient after the procedure is complete. Once the procedure is complete, the rod cutter assembly 100 can then be disassembled so that the blade members 102, 104 and associated pins 106, 140, 144 coupling the blade members 102, 104 to the actuator tool 120 are disposed of and the actuator tool 120 and leveraging member 158 are reused in subsequent procedures. The rod cutter assembly 100 as provided herein allows for a surgeon to place the rod 164 once and cut the rod 164 to length in place (in-situ), without having to iteratively place, measure, and remove the rod, cutting it to length after each measurement. Further, by having the blade members 102, 104 be replaceable for each procedure ensures that the blade members 102, 104 are sufficiently sharp before the procedure begins and eliminates the need for sharpening the tools after the procedure is complete.

Figure 13A:
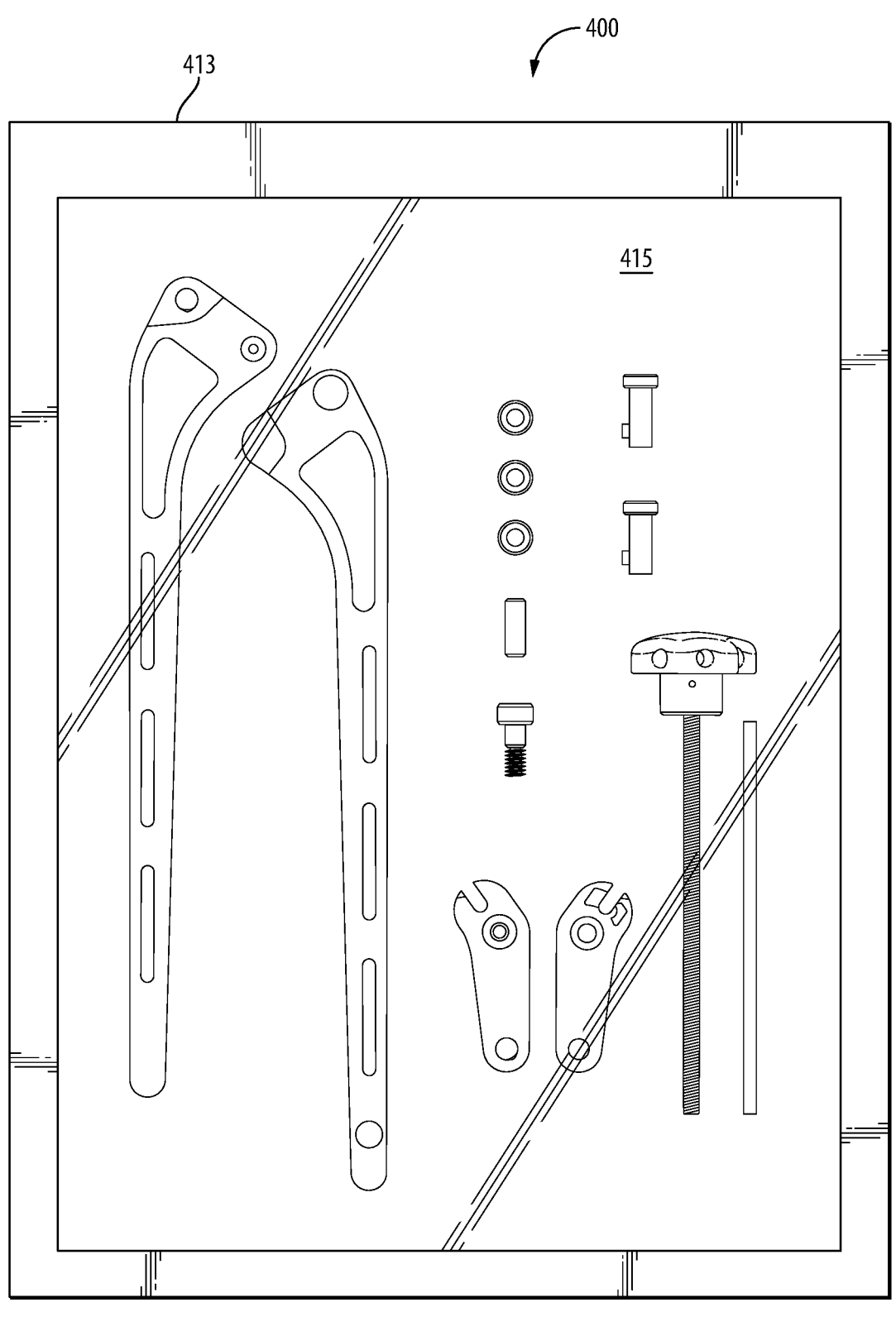
FIG. 13A is a perspective view of an embodiment of a kit constructed in accordance with the present disclosure, showing an in-situ rod cutter assembly in a disassembled state and within a sterile pack.
Figure 13B:
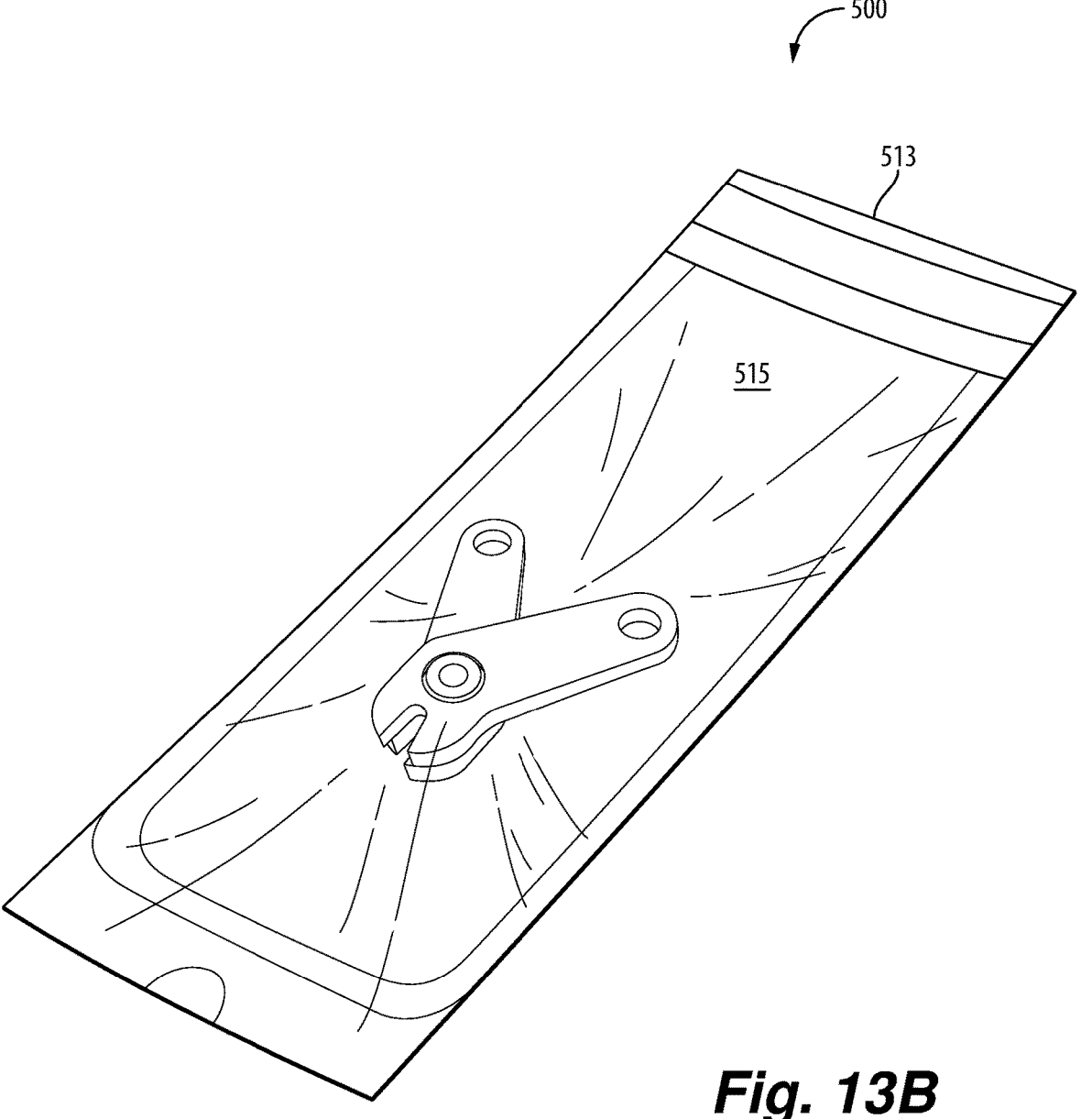
FIG. 13B is a perspective view of an embodiment of a kit constructed in accordance with the present disclosure, showing a blade assembly of an in-situ rod cutter assembly within a sterile pack.

As shown in FIG. 13A, in accordance with at least one aspect of this disclosure, a kit 400 can include a package 413 having a sterile interior 415. The package 415 can enclose a first blade member (e.g., blade member 102) and a second blade member (e.g., blade member 104). The first and second blade members in the package 413 can be the same or similar to those described above with respect to assembly 100. In certain embodiments, the first and second blade members can be identical to one another. The package 413 can include a pair of ball detent pins (e.g., linkage pins 140, 144), configured to join the first and second blade members to an actuator tool (e.g., actuator tool 120). In embodiments, the actuator tool can also be enclosed in the package. In certain embodiments, the ball detent pins can be included on the handle portions within the sterile pack. In embodiments, a leveraging member (e.g., leveraging tool 158) can be included in the package configured to engage a threaded rod knob (e.g., knob 154) of the actuator tool to provide leverage for actuating the first and second blade members. As shown in FIG. 13B, in the kit 500, the package 513 can include only a pair of blade members (e.g., blade members 102, 104) pre-assembled, within the sterile interior 415, the pre-assembled blade members configured to attach to an existing rod cutter assembly handle portions. In this case, the hand portions can be sterilized and be reused, while the blade members are discarded after the procedure.

The methods and systems of the present disclosure, as described above and shown in the drawings, provide for improved efficiency and accuracy when placing stabilizing rods between vertebrae in an orthopedic surgical procedure. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A surgical rod cutter assembly comprising:
a first blade member including a first open notch in a first end thereof, wherein the first open notch spans across a first ingress axis, wherein there is a first rotation bore defined through the first blade member, wherein a linkage of the first blade member extends away from the rotation bore on a longitudinal axis of the first linkage, and wherein the first rotation bore intersects the longitudinal axis of the first linkage;
a second blade member including a second open notch in a first end thereof, wherein the second open notch spans across a second ingress axis, wherein there is a second rotation bore defined through the second blade member, wherein a linkage of the second blade member extends away from the second rotation bore on a longitudinal axis of the second linkage, and wherein the second rotation bore intersects the longitudinal axis of the second linkage; and
a fulcrum pin engaged through the first and second rotation bores to rotationally engage the first and second blade members together wherein:
in an open position, the first and second ingress axes are aligned with one another to admit a rod therealong into the first and second open notches for cutting, and the first and second linkage axes are angled to a narrow position relative to one another and wherein:
in a closed position, the first and second ingress axes are angled relative to one another, and, the first and second linkage axes are angled at a widened position relative to the narrow position,
wherein the first blade member includes a first pawl extending into a pocket of the second blade member, wherein in the closed position, the first pawl cooperates with the terminal surface of the second open notch to form a capture pocket configured to capture a cut rod piece after cutting the rod.

2. The assembly as recited in claim 1, wherein in both the open position and in the closed position, the first and second ingress axes both pass through a rotation axis that extends along the fulcrum pin.

3. The assembly as recited in claim 1, wherein the first open notch includes:
a first notch surface on one side of the first ingress axis;
a second notch surface opposite the first notch surface across the first ingress axis, and
a terminal surface connecting between the first and second notch surfaces, terminating the first open notch along the first ingress axis, wherein the first open notch defines an opening between the first and second notch surfaces that opens away from the fulcrum pin.

4. The assembly as recited in claim 3, wherein the first and second notch surfaces of the first open notch are parallel to one another, and wherein the terminal surface of the first open notch is semi-cylindrical.

5. The assembly as recited in claim 3, wherein the second open notch includes:
a first notch surface on one side of the second ingress axis;
a second notch surface opposite the first notch surface across the second ingress axis; and
a terminal surface connecting between the first and second notch surfaces, terminating the second open notch along the second ingress axis,
wherein the second open notch defines an opening between the first and second notch surfaces that opens away from the fulcrum pin.

6. The assembly as recited in claim 5, wherein the first and second notch surfaces of the second open notch are parallel to one another, and wherein the terminal surface of the second open notch is semi-cylindrical.

7. The assembly as recited in claim 5, wherein in the open position, the first notch surface of the first open notch is aligned parallel with the first notch surface of the second open notch, and the second notch surface of the first open notch is aligned parallel with the second notch surface of the second open notch.

8. The assembly as recited in claim 1, wherein in the closed position, the first and second ingress axes are angled obliquely relative to one another.

9. The assembly as recited in claim 8, wherein in the closed position, the first and second open notches are misaligned for holding a cut rod piece.

10. The assembly as recited in claim 1, wherein the second blade member includes a second pawl extending into a pocket of the first blade member, wherein in the closed position, the second pawl cooperates with the terminal surface of the first open notch to form a capture pocket configured to capture a cut rod piece after cutting a rod.

11. The assembly as recited in claim 10, further comprising and actuator tool having:
a first linkage including a first handle portion, a first main pin bore, and a first linkage bore; and
a second linkage including a second handle portion, a second main pin bore, and a second linkage bore,
wherein the first and second linkages are joined to one another by a main pin engaged through the first and second main pin bores for relative rotation,
wherein the first linkage is pinned with a first linkage pin that passes through the first linkage bore and a corresponding bore of the first blade member, and
wherein the second linkage is pinned with a second linkage pin that passes through the second linkage bore and a corresponding bore of the second blade member.

12. The assembly as recited in claim 11, wherein the first linkage pin is removably engaged to the first linkage and to the first blade member with a movable detent ball in the first linkage pin, and wherein the second linkage pin is removably engaged to the second linkage and to the second blade member with a movable detent ball in the second linkage pin.

13. The assembly as recited in claim 11, further comprising a threaded rod connecting the first handle portion to the second handle portion, wherein a knob is operatively connected to the threaded rod to actuate the first and second linkages between the first and second positions.

14. The assembly as recited in claim 13, wherein the knob includes leveraging bores configured to receive a lever arm to facilitate rotation of the knob.

15. The assembly as recited in claim 1, further comprising a bearing washer extending around the fulcrum pin and rotatably engaged to inward facing bearing surfaces of each of the first and second blade members.

16. The assembly as recited in claim 15, further comprising:

a first outside washer engaged to the fulcrum pin and an outer surface of the first blade member; and a second outside washer engaged to the fulcrum pin and an outer surface of the second blade member.

17. A kit comprising:

a package having a sterile interior enclosing:

a first blade member including a first open notch in a first end thereof, wherein the first open notch spans across a first ingress axis, wherein there is a first rotation bore defined through the first blade member, wherein a linkage of the first blade member extends away from the rotation bore on a longitudinal axis of the first linkage, and wherein the first rotation bore intersects the longitudinal axis of the first linkage;

a second blade member including a second open notch in a first end thereof, wherein the second open notch spans across a second ingress axis, wherein there is a second rotation bore defined through the second blade member, wherein a linkage of the second blade member extends away from the second rotation bore on a longitudinal axis of the second linkage, and wherein the second rotation bore intersects the longitudinal axis of the second linkage; and a fulcrum pin configured to be engaged through the first and second rotation bores to rotationally engage the first and second blade members together wherein:

in an open position, the first and second ingress axes are aligned with one another to admit a rod therealong into the first and second open notches for cutting, wherein the first and second linkage axes are angled to a narrow position relative to one another in the open position, and wherein:

in a closed position, the first and second ingress axes are angled relative to one another, and wherein in the closed position, the first and second linkage axes are angled at a widened position relative to the narrow position, wherein the first blade member includes a first pawl extending into a pocket of the second blade member, wherein in the closed position, the first pawl cooperates with the terminal surface of the second open notch to form a capture pocket configured to capture a cut rod piece after cutting the rod.

18. The kit as recited in claim 17, further comprising a pair of ball detent pins in the package, configured to join the first and second blade members to an actuator tool.

19. The kit as recited in claim 18, further comprising the actuator tool in the package.

20. The kit as recited in claim 19, further comprising a leveraging member in the package configured to engage a threaded rod knob of the actuator tool to provide leverage for actuating the first and second blade members.

* * * * *